(12) United States Patent
Dorian et al.

(10) Patent No.: US 7,837,884 B2
(45) Date of Patent: *Nov. 23, 2010

(54) METHODS AND APPARATUS FOR ISOLATING PLATELETS FROM BLOOD

(75) Inventors: Randel Dorian, San Diego, CA (US); Scott R. King, San Francisco, CA (US); Richard Wood Storrs, Berkeley, CA (US)

(73) Assignee: Hanuman, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/344,895

(22) Filed: Dec. 29, 2008

(65) Prior Publication Data

US 2009/0101599 A1    Apr. 23, 2009

Related U.S. Application Data

(60) Division of application No. 11/584,414, filed on Oct. 19, 2006, now Pat. No. 7,470,371, which is a continuation of application No. 11/108,387, filed on Apr. 18, 2005, now Pat. No. 7,223,346, which is a continuation of application No. 10/176,272, filed on Jun. 18, 2002, now abandoned.

(60) Provisional application No. 60/377,559, filed on May 3, 2002, provisional application No. 60/379,951, filed on May 10, 2002, provisional application No. 60/382,639, filed on May 21, 2002.

(51) Int. Cl.
| | |
|---|---|
| C02F 1/38 | (2006.01) |
| B04B 1/04 | (2006.01) |
| B04B 1/06 | (2006.01) |
| B04B 3/02 | (2006.01) |
| B04B 1/00 | (2006.01) |

(52) U.S. Cl. ............... 210/787; 210/109; 210/121; 210/512.1; 210/516; 210/518; 210/361; 210/789; 422/102; 422/918; 436/177; 494/16; 494/37; 494/38; 494/45; 494/56

(58) Field of Classification Search .............. None
See application file for complete search history.

(56) References Cited

U.S. PATENT DOCUMENTS 280,820 A    7/1883    Hickson et al.

(Continued)

FOREIGN PATENT DOCUMENTS

AU    696278    1/1999

(Continued)

OTHER PUBLICATIONS

Anesthesiology, vol. 81, No. 4, pp. 1074-1077, Oct. 1994, Hiromasa Mitsuhata, M.D., et al., "An Anaphylactic Reaction to Topical Fibrin Glue".

(Continued)

*Primary Examiner*—Krishnan S Menon
(74) *Attorney, Agent, or Firm*—Harness, Dickey

(57) ABSTRACT

A platelet collection device comprising a centrifugal spin-separator container with a cavity having a longitudinal inner surface. A float in the cavity has a base, a platelet collection surface above the base, an outer surface. The float density is below the density of erythrocytes and above the density of plasma. The platelet collection surface has a position on the float which places it below the level of platelets when the float is suspended in separated blood. During centrifugation, a layer of platelets or buffy coat collects closely adjacent the platelet collection surface. Movement of a float having a density greater than whole blood through the sedimenting erythrocytes releases entrapped platelets, increasing the platelet yield.

17 Claims, 6 Drawing Sheets

U.S. PATENT DOCUMENTS

| | | |
|---|---|---|
| 593,333 A | 11/1897 | Park |
| 1,468,313 A | 9/1923 | Lux |
| 1,593,814 A | 7/1926 | Vogel |
| 2,553,004 A | 5/1951 | Rabatine |
| 3,409,165 A | 11/1968 | Creith |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,723,244 A | 3/1973 | Breillatt, Jr. |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,896,733 A | 7/1975 | Rosenberg |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,941,699 A | 3/1976 | Ayres |
| 3,951,801 A | 4/1976 | Ayres |
| 3,957,654 A | 5/1976 | Ayres |
| 3,972,812 A | 8/1976 | Gresl, Jr. |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A * | 4/1984 | Wells ......................... 210/782 |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,735,616 A | 4/1988 | Eibl et al. |
| 4,735,726 A | 4/1988 | Duggins |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,844,818 A | 7/1989 | Smith |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,902,281 A | 2/1990 | Avoy |
| 4,909,251 A | 3/1990 | Seelich et al. |
| 4,917,801 A | 4/1990 | Luderer et al. |
| 4,928,603 A | 5/1990 | Rose et al. |
| 4,929,242 A | 5/1990 | Desecki et al. |
| 4,939,081 A | 7/1990 | Figdor et al. |
| 4,943,273 A | 7/1990 | Pages et al. |
| 4,946,601 A | 8/1990 | Fiehler |
| 4,957,637 A | 9/1990 | Cornell |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |

| Patent | Date | Inventor |
|---|---|---|
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,733,466 A | 3/1998 | Benebo et al. |
| 5,733,545 A | 3/1998 | Hood, III |
| 5,736,033 A | 4/1998 | Coleman et al. |
| 5,738,796 A | 4/1998 | Bormann et al. |
| 5,750,025 A | 5/1998 | Holmes et al. |
| 5,785,700 A | 7/1998 | Olson |
| 5,786,217 A | 7/1998 | Tubo et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,860,937 A | 1/1999 | Cohen |
| 5,863,892 A | 1/1999 | Stern et al. |
| 5,865,785 A | 2/1999 | Bischof |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,980,734 A | 11/1999 | Itoh et al. |
| 6,010,627 A | 1/2000 | Hood, III |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |

| | | |
|---|---|---|
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,342,157 B1 | 1/2002 | Hood, III |
| 6,351,659 B1 | 2/2002 | Vilsmeier |
| 6,368,298 B1 | 4/2002 | Beretta et al. |
| 6,398,972 B1 | 6/2002 | Blasetti et al. |
| 6,406,671 B1 | 6/2002 | DiCesare et al. |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,472,162 B1 | 10/2002 | Coelho et al. |
| 6,508,778 B1 | 1/2003 | Verkaart et al. |
| 6,516,953 B1 | 2/2003 | DiCesare et al. |
| 6,544,162 B1 | 4/2003 | Van Wie et al. |
| 6,558,341 B1 | 5/2003 | Swisher |
| 6,596,180 B2 | 7/2003 | Baugh et al. |
| 6,629,919 B2 | 10/2003 | Egozy et al. |
| 6,676,629 B2 | 1/2004 | Andrew et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,777,231 B1 | 8/2004 | Katz et al. |
| 6,803,022 B2 * | 10/2004 | DiCesare et al. ............ 422/101 |
| 6,811,777 B2 | 11/2004 | Mishra |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E * | 7/2005 | Wells et al. ................... 494/20 |
| 7,011,644 B1 | 3/2006 | Andrew et al. |
| 7,077,273 B2 | 7/2006 | Ellsworth et al. |
| 7,179,391 B2 | 2/2007 | Leach et al. |
| 7,223,346 B2 | 5/2007 | Dorian et al. |
| 7,470,371 B2 | 12/2008 | Dorian et al. |
| 2001/0009757 A1 | 7/2001 | Bischof et al. |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2005/0076396 A1 | 4/2005 | Katz et al. |
| 2005/0084961 A1 | 4/2005 | Hedrick et al. |
| 2005/0109716 A1 | 5/2005 | Leach et al. |
| 2005/0130301 A1 | 6/2005 | McKay et al. |
| 2005/0153441 A1 | 7/2005 | Hedrick et al. |
| 2005/0153442 A1 | 7/2005 | Katz et al. |
| 2005/0196874 A1 | 9/2005 | Dorian et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0083720 A1 | 4/2006 | Fraser et al. |
| 2006/0196885 A1 | 9/2006 | Leach et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2008/0217264 A1 | 9/2008 | Leach et al. |
| 2008/0217265 A1 | 9/2008 | Leach et al. |
| 2008/0283474 A1 | 11/2008 | Leach et al. |
| 2009/0014391 A1 | 1/2009 | Leach et al. |
| 2009/0221075 A1 | 9/2009 | Dorian et al. |

FOREIGN PATENT DOCUMENTS

| | | |
|---|---|---|
| BR | 9103724 | 3/1993 |
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1006360 | 6/2000 |
| EP | 1005910 | 7/2000 |
| EP | 1289618 | 3/2003 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 | 12/1985 |
| JP | 2036872 | 2/1990 |
| JP | 02071747 | 3/1990 |
| JP | 02129224 | 10/2000 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-1996017871 | 6/1996 |
| WO | WO-00061256 | 10/2000 |
| WO | WO-0103756 | 1/2001 |
| WO | WO-0183068 | 11/2001 |
| WO | WO-0238610 | 5/2002 |
| WO | WO-02060925 | 8/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03092894 | 11/2003 |
| WO | WO-03099412 | 12/2003 |
| WO | WO-04009207 | 1/2004 |
| WO | WO-2004104553 | 12/2004 |

| WO | WO-2005034843 A2 | 4/2005 |
| WO | WO-2007142908 A1 | 12/2007 |

OTHER PUBLICATIONS

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Bang, N. U., et al., "Plasma Protein Requirements for Human Platelet Aggregation" Ann. N. Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (3 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac, Cardiovasc Surg* 105 (5 1993): 892-7.

Biopolymers, vol. 27, pp. 763-774, 1988, Gerald Marx, "Mechanism of Fibrin Coagulation Based on Selective, Cation-Driven, Protofibral Association".

Brodke, et al., "Bone Grafts Prepared with Selective Cell Retention Technology Heal Canine Segmental Defects as Effectively as Autograft", SCR-Enriched Bone Crafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (7 1992): 641-3.

Clotalyst™ Automatic Clotting Factor, Would you like to have an autologous thrombin for rapid clotting and haemostasis?, brochure, Biomet Biologics, Inc., Feb. 2007, (12 pages).

Collier, B.S. et al., "The pH Dependence of Quantitative Ristocetin-induced Platlet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May), 1976.

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

DelRossi, A. J., A. C. Cernaianu, R. A. Vertrees, C. J. Wacker, S. J. Fuller, J. Cilley Jr., and W. A. Baldino. "Platlet-rich plasma reduces postoperative blood loss after cardioplumonary bypass." *J Thorac Cardiovasc Surg* 100 (2 1990): 281-6.

Drug Intelligence and Clinical Pharmacy, vol. 22, pp. 946-952, Dec. 1988, Dennis F. Thompson et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992).

Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (8 1990):741-7.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS®II System, Gravitational Platelet Separation System, "Accelerating the Body's Natural i Healing Process," Cell Factor Technologies, Inc., Biomet Europe (2005) 16 pages, http://www.cellfactortech.com/global_products.cfm, printed Sep. 16, 2005.

GPS®II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, Jan. 22, 2004.

Harris, E.L.V. Concentration of the Extract. In. Protein Purification Methods: A Practical Approach Harris, E.L.V.; Angel, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992): 357-9.

Harvest Technologies brochure, SmartPrep2 (2002).

Hennis, H. L., W. C. Stewart, and E. K. Jeter. "Infectious disease risks of fibrin glue [letter]." *Ophthalmic Surg* 23 (9 1992): 640.

International Search Report and Written Opinion mailed Jul. 2, 2008 for International Application No. PCT/US2008/004687 which claims priority to U.S. Appl. No. 60/911,407, filed Apr. 12, 2007.

International Search Report for International Application No. PCT/US/03 16506 mailed Oct. 13, 2003 which claims benefit of U.S. Appl. No. 60/383,013, filed May 24, 2002.

International Search Report for International Application No. PCT/US2007/012587 mailed Nov. 6, 2007 which claims benefit of U.S. Appl. No. 11/441,276, filed May 25, 2006.

Jackson, C. M. and Y. Nemerson. "Blood coagulation." *Annu Rev Biochem* 49 (811 1980): 765-811).

Jorgensen, et al., "Stem Cells for Repair of Cartilage and Bone: The Next Challenge in Osteoarthritis and Rheumatoid Arthritis," Annals of Rheumatic Diseases, Aug. 2000.

Journal of Oral Maxillofacial Surgery, vol. 43, pp. 605-611, 1985, Helene Matras, M.D., "Fibrin Seal: The State of the Art".

Karpatkin, S., "Heterogeneity of Human Platelets. VI., Correlation of Platelet Function with Platelet Volume", Blood, vol. 51, No. 2 (Feb. 1978).

Kjaergard, H. K., U. S. Weis-Fogh, H. Sorensen, J. Thiis, and I. Rygg. "A simple method of preparation of autologous fibrin glue by means of ethanol." *Surg Gynecol Obstet* 175 (1 1992): 72-3.

Kjaergard, H. K., Fogh Us Weis, and J. J. Thiis. "Preparation of autologous fibrin glue from pericardial blood." *Ann Thorac* Sur 55 (2 1993): 543-4.

Laryngoscope vol. 99, pp. 974-976, Sep. 1989, Kyosti Laitakari, M.D., et al., ,"Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lasher, Lisa, M.D., "My Experience with PRP," PowerPoint presentation, http://www.cellfactortech.com/global_products.cfm, printed Sep. 16, 2005.

Lerner, R. and N. S. Binur. "Current status of surgical adhesives." *J Surq Res* 48 (2 1990): 165-81.

Lu, et al., "Bone Marrow Mesenchymal Stem Cells: Progress in Bone/Cartilage Defect Repair," 19(1), Jan. 2002.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).

Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).

Minntech®, Filtration Technologies Group, "Renaflo® II Hemofilter," Minntech Corporation (2004); http://www.minntech.com/ftg/products/renaflo/index.html, printed Jul. 15, 2004 (2 pages).

Molnar, Amy, "Stem Cells from Muscles Can Repair Cartilage, Study Finds Genetically Engineered Muscle-Derived Stem Cells Improved Cartilage Repair in Rats", American College of Rheumatology, (2005).

Moretz, W., Jr., J Shea Jr., J. R. Emmett, and J Shea. "A simple autologous fibrinogen glue for otologic surgery." *Otolaryngol Head Neck Sur.* 95 (1 1986): 122-4.

Nilsson, et al., "Bone Repair Induced by Bone Morphogenetic Protein in Ulnar Defects in Dogs," The Journal of Bone and Joint Surgery, vol. 68 B., No. 4, Aug. 1986.

Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Sanal, M. "Does fibrin glue cause foreign body reactions? [letter]." *Eur J Pediatr Surg* 3 (3 1993): 190 (1 page).

Sanal, M., H. Dogruyol, A. Gurpinar, and O. Yerci. "Does fibrin glue cause foreign body reactions?" *Eu r J Pediatr Surg* 2 (5 1992): 285-6.

Schmidt, K.G., et al., "Labelling of Human and Rabbit Platelets with Indium-Oxine Complex", 123:97-106 (1979).

Schmidt, K.G., et al., "Preparation of Platelet Suspensions from Whole Blood in Buffer", Scand. J. Hoemato, 23:88-96 (1979).

Sierra, D. H. "Fibrin sealant adhesive systems: a review of their chemistry, material properties and clinical applications." *J Biomater Appl* 7 (4 1993): 309-52.

'Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Vox Sanquinis, vol. 68: 82-89, Feb. 1995, Boomgaard et. al, Pooled Platelet Concentration Prepred by the Weis-Fogh, U. S. "Fibrinogen prepared from small blood samples for autologous use in a tissue adhesive system." *Eur Surg* Res 20 (5-6 1988): 381-9.

Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W.B. Saunders Company, 1992).

Written Opinion of the interantional Preliminary Examining Authority mailed Mar. 17, 2009, for International Application No. PCT/US2008/004687 which claims priority to U.S. Appl. No. 60/911,407, filed Apr. 12, 2007.

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

DeUgarte, M.D., Daniel A., et al., "Future of Fat as Raw Material for Tissue Regneration," (2007) pages 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

Guilak, Frank, et al., "Adipose-derived adult stem cells for cartilage tissue engineering," Biorheology 41 (2004) pp. 389-399, IOS Press.

Hattori, et al., "Osteogenic Potential of Human Adipose Tissue-Derived Stromal Cells as an Alternative Stem Cell Source," Cells Tissues Organs (2004) 178:2-12 Karger.

International Preliminary Report on Patentability completed Aug. 13, 2009 for PCT/US2008/004687 claiming benefit of U.S. Appl. No. 60/911,407, filed Apr. 12, 2007.

International Search Report and Written Opinion mailed Jul. 3, 2009 for PCT/US2009/035564 claiming benefit of U.S. Appl. No. 61/078,178, filed Jul. 3, 2008.

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Parker, Anna M., et al., Adipose-derived stem cells for the regeneration of damaged tissues, Expert Opinion, Cell-& Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sigma-Aldrich® Alkaline Phosphatase (Procedure No. 85), drug fact sheet, (2003) pp. 1-2, Sigma-Aldrich, Inc.

Takahashi, Kazutoshi et al., "Induction of Pluripotent Stem Cells from Adult Human Fibroblasts by Defined Factors," Cell, (2007) pp. 1-12, Elsevier Inc.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

"Trypsinizing cells." Bart's Cookbook, Web. Apr. 14, 2010. http://pingu.salk.edu/~sefton/Hyper_protocols/trypsin.html.

Jayadev, Suprya. "Trypsinization of Adherent Cells." Aug. 8, 1991. Web. Apr. 14, 2010. http://www.duke.edu/web/ceramide/protocols/0005.html.

Ponticiello, Michael S., "A Rapid Technique for the Isolation and Concentration of Stem Cells from Human Bone Marrow", Cell Factor Technologies, Inc. (2006) 2 pages.

* cited by examiner

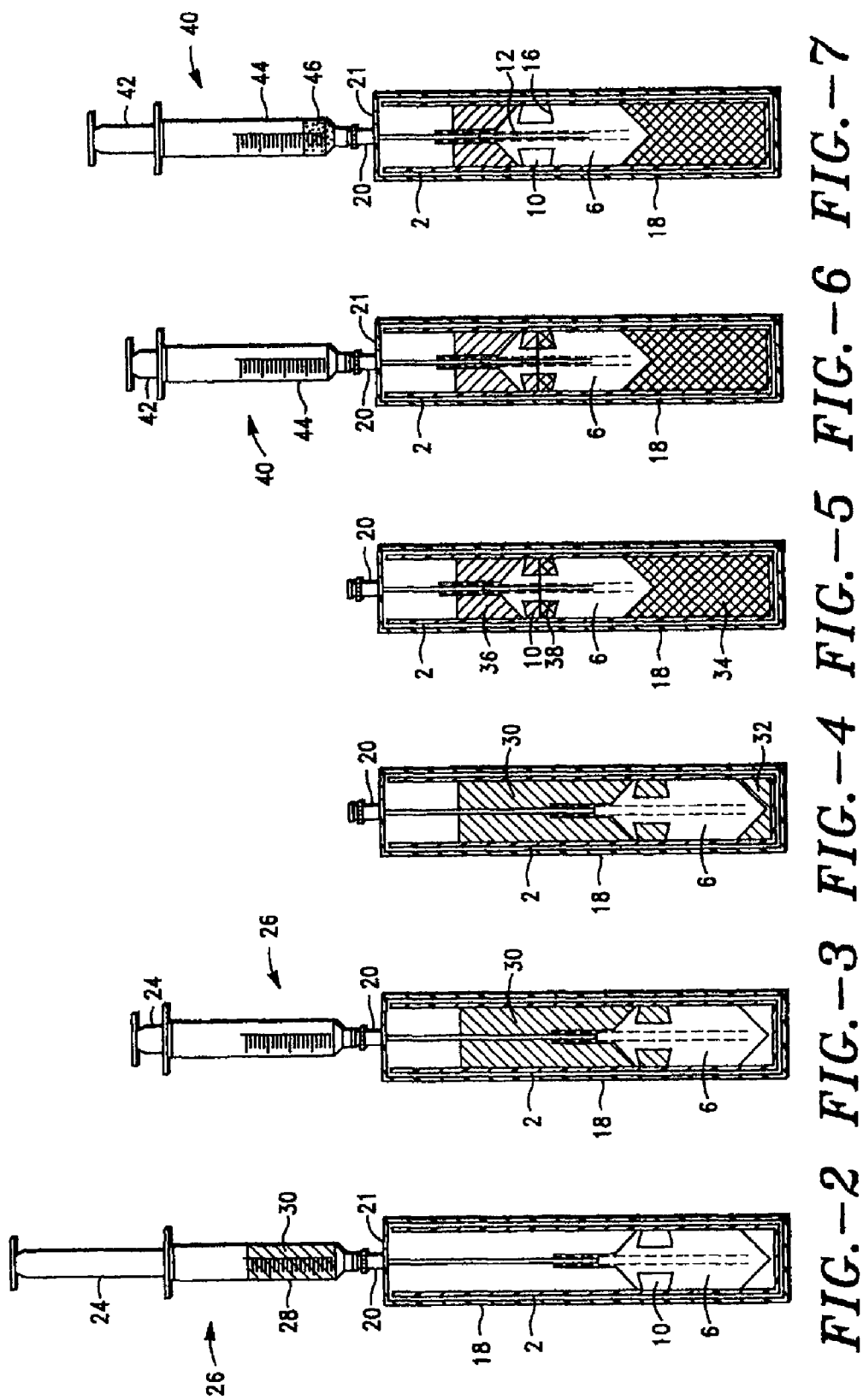

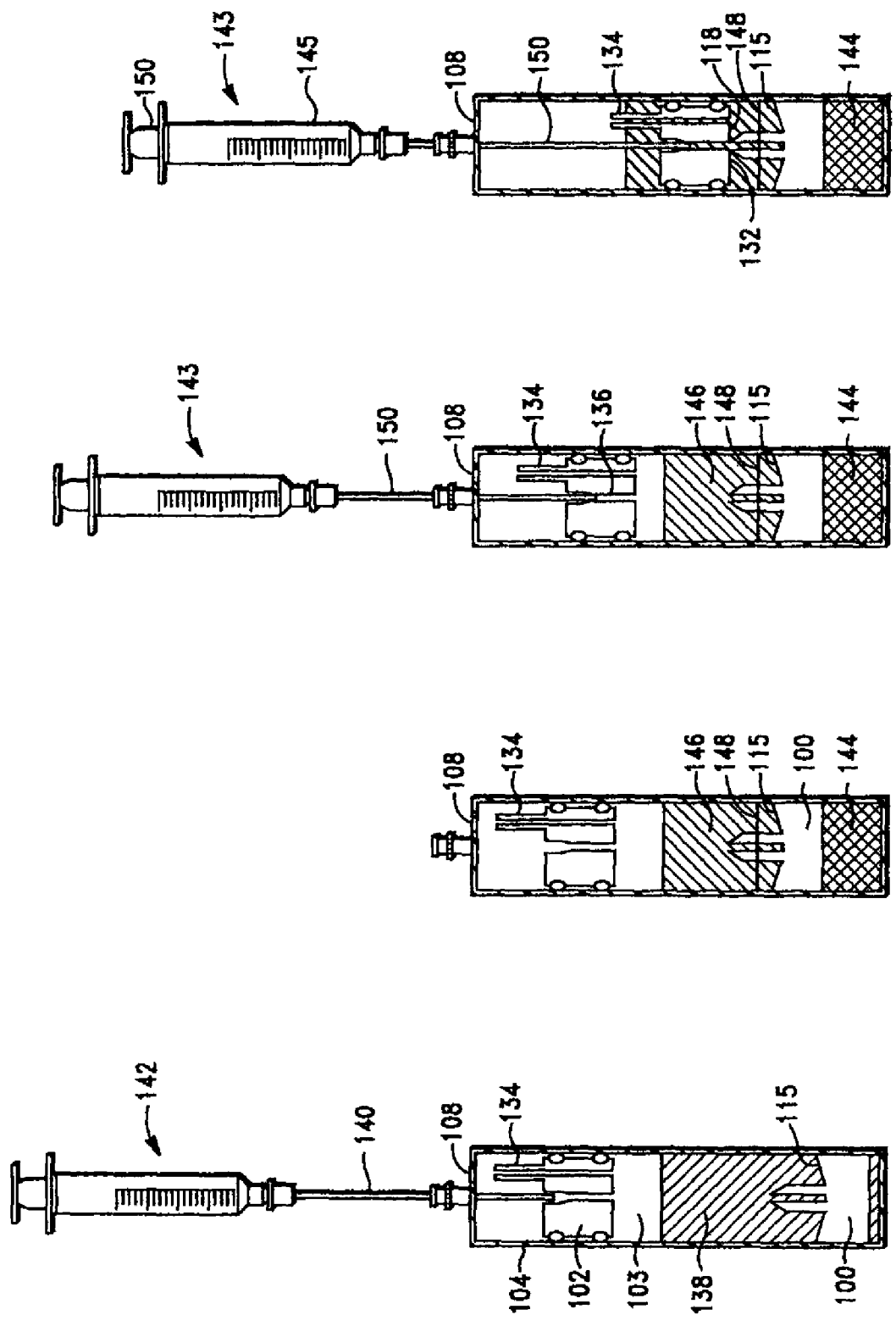

METHODS AND APPARATUS FOR ISOLATING PLATELETS FROM BLOOD

CROSS-REFERENCE TO RELATED APPLICATIONS

This application is a divisional of U.S. patent application Ser. No. 11/584,414 filed on Oct. 19, 2006; now U.S. Pat. No. 7,470,371; which is a continuation of U.S. patent application Ser. No. 11/108,387 filed on Apr. 18, 2005, now U.S. Pat. No. 7,223,346; which is a continuation of U.S. patent application Ser. No. 10/176,272 filed on Jun. 18, 2002, now abandoned; which claims benefit of all of U.S. Prov. App. No. 60/377,559, filed on May 3, 2002; U.S. Prov. App. No. 60/379,951, filed on May 10, 2002; and U.S. Prov. App. No. 60/382,639, filed on May 21, 2002. The entire disclosures of all the above applications are incorporated herein by reference.

BACKGROUND

The present invention concerns apparatuses and methods for rapid fractionation of blood into erythrocyte, plasma and platelet fractions. Each fraction may be put to use or returned to the blood donor. Useful high concentration platelet fractions have platelet concentrations in excess of two times the concentration in anti-coagulated whole blood before processing of greater than $2 \times 10^6$ platelet/µL. The invention has particular value for rapid preparation of autologous concentrated platelet fractions to help or speed healing.

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

Under the influence of gravity or centrifugal force, blood spontaneously sediments into three layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen).

The bottom, high-density layer is a deep red viscous fluid comprising a nuclear red blood cells (erythrocytes) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

The intermediate layer is the smallest, appearing as a thin white band on top the erythrocyte layer and below the plasma, and is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in the blood vessels to stop bleeding and deliver growth and wound healing factors to the wound site.

Extraction of Platelets

Extraction of platelets from whole blood has been reviewed (Pietersz 2000). In transfusion medicine the intention is to transfuse each patient only with the component that is needed, so the aim of blood centers is to manufacture blood components as pure as possible, that is with the least contaminating cells. Platelets are the most difficult to isolate and purify. Based on data from Pietersz (2000), even under optimal conditions of centrifugation (long time at low speed), a significant fraction of platelets remain trapped within the sedimented erythrocytes.

Through the years centrifugation methods have been developed to separate the platelets from red blood cells, white blood cells and plasma. These methods separate the components both in plastic bag systems and in apheresis devices, and more recently in specialized apparatuses. Historically most platelet concentrates have been harvested from donors and used to treat thrombocytopenia, i.e., allogenically. More recently the platelet concentrates have been used to promote wound healing, and the use of autologous platelet concentrates (sequestration of platelets for treatment of the platelet donor) has grown.

The sedimentation of the various blood cells and plasma is based on the different specific gravity of the cells and the viscosity of the medium. This may be accelerated by centrifugation according approximately to the Svedberg equation:

$$V = ((2/9) \omega^2 R (d_{cells} - d_{plasma}) r^2) / \eta_t$$

where

V=sedimentation velocity,

ω=angular velocity of rotation,

R=radial distance of the blood cells to the center of the rotor, d=specific gravity, r=radius of the blood cells, $\eta_t$=viscosity of the medium at a temperature of t° C.

Characteristics of blood components are shown in Table 1.

TABLE 1

| Component | Diameter (µm) | Specific gravity (g/ml) | Deformability | Adhesion |
|---|---|---|---|---|
| Red Cells | 5.4 | 1.100 | +++ | − |
| Granulocytes | 9.6 | 1.085 | + | ++ |
| Lymphocytes | 7.6 | 1.070 | ± | ± |
| Monocytes | 11.2 | 1.063 | ± | ± |
| Platelets | 3.2 | 1.058 | ± | +++ |
| Plasma | NA | 1.026 | NA | NA |
| Additive Solution | NA | 1.007 | NA | NA |

When sedimented to equilibrium, the component with the highest specific gravity (density) eventually sediments to the bottom, and the lightest rises to the top. But the rate at which the components sediment is governed roughly by the Svedberg equation; the sedimentation rate is proportional to the square of the size of the component. In other words, at first larger components such as white cells sediment much faster than smaller components such as platelets; but eventually the layering of components is dominated by density.

Soft Spin Centrifugation

When whole blood is centrifuged at a low speed (up to 1,000 g) for a short time (two to four minutes) white cells sediment faster than red cells and both sediment much faster than platelets (per Svedberg equation above). At higher speeds the same distribution is obtained in a shorter time. This produces layers of blood components that are not cleanly separated and consist of (1) plasma containing the majority of the suspended platelets and a minor amount of white cells and red cells, and (2) below that a thick layer of red cells mixed with the majority of the white cells and some platelets. The method of harvesting platelet-rich plasma (PRP) from whole blood is based on this principle. The term "platelet-rich" is used for this component because most of the platelets in the whole blood are in the plasma following slow centrifugation so the concentration of platelets in the plasma has increased. Centrifugal sedimentation that takes the fractionation only as far as separation into packed erythrocytes and PRP is called a "soft spin". "Soft spin" is used herein to describe centrifugation conditions under which erythrocytes are sedimented but platelets remain in suspension. "Hard spin" is used herein to describe centrifugation conditions under which erythrocytes sediment and platelets sediment in a layer immediately above the layer of erythrocytes.

Two Spin Platelet Separation

Following a soft spin, the PRP can removed to a separate container from the erythrocyte layer, and in a second centrifugation step, the PRP may be fractioned into platelet-poor plasma (PPP) and platelet concentrate (PC). In the second spin the platelets are usually centrifuged to a pellet to be re-suspended later in a small amount of plasma.

In the most common method for PRP preparation, the centrifugation of whole blood for 2 to 4 min at 1,000 g to 2,500 g results in PRP containing the majority of the platelets. After the centrifugation of a unit (450 ml) of whole blood in a 3-bag system the PRP is transferred to an empty satellite bag and next given a hard spin to sediment the platelets and yield substantially cell-free plasma. Most of the platelet poor plasma (PPP) is removed except for about 50 ml and the pellet of platelets is loosened and mixed with this supernatant. Optionally one can remove about all plasma and reconstitute with additive solution. To allow aggregated platelets to recover the mixture is given a rest of one to two hours before platelets are again re-suspended and then stored on an agitator.

It is believed that centrifugation can damage the platelets by sedimenting the platelets against a solid, non-physiological surface. The packing onto such a surface induces partial activation and may cause physiological damage, producing "distressed" platelets which partially disintegrate upon re-suspension.

Hard Spin Centrifugation

If the centrifugation is continued at a low speed the white cells will sediment on top of the red cells whereas the platelets will remain suspended in the plasma. Only after extended low speed centrifugation will the platelets also sediment on top of the red cells.

Experiments with a blood processor (deWit, 1975) showed that centrifugation at a high speed (2,000 g-3,000 g) produces a similar pattern of cell separation in a shorter time. Initially the cells separate according to size, i.e., white cells sediment faster than red cells and platelets remain in the plasma. Soon the red cells get 'packed' on each other squeezing out plasma and white cells. Because of their lower density, white cells and platelets are pushed upwards to the interface of red cells and plasma whereas the platelets in the upper plasma layer will sediment on top of this interface, provided the centrifugal force is sufficiently high and sedimentation time is sufficiently long. Plasma, platelets, white cells and red cells will finally be layered according to their density. Platelets sedimented atop a layer of red cells are less activated than those isolated by the "two spin" technique.

Platelet Yields and Centrifuge Speed

The so called "buffy coat" consists of the layers of platelets and white cells (leukocytes) but is usually harvested along with the lower part of the plasma layer and the upper layer of the red cell mass. In this application, all references to the platelet layer are intended to mean the platelet layer if no leukocytes are present or to the buffy coat layer when leukocytes are present mixed with the platelets.

The process and method of this invention can accomplish platelet isolation and collection with a wide range including both low and high centrifugation forces. Effective separation does not require a high g centrifugation; good results have been obtained with 600 g-1000 g or low speed centrifugation. High speed centrifugation refers to centrifugal forces greater than 2000 g. Experiments have shown that long (30-45 min) centrifugation at a force of about 700 g gives the most complete separation of whole blood into components. Such long times are not considered to be practical and economical for intra-operative autologous applications. For buffy coat separation one can spin 7 to 10 min at about 3,000 g to enable separation of whole blood into cell-free plasma, a buffy coat containing 60-70% of the white cells and 70-80% of the platelets, and red cells contaminated with approximately 30% of the white cells and 10-20% of the platelets.

Apheresis—Single Spin Platelet Separation

Specialized apparatuses have been invented to perform apheresis, the separation of platelets from blood while re-infusing the other components into the donor. This permits donors to give more platelets than possible with the two-step centrifugation because loss of erythrocytes limits the volume of blood that blood donors may give. Typically, a two to three hour apheresis procedure will produce a platelet product containing $3 \times 10^{11}$ platelets, equivalent to 6 or more conventional blood donations.

The first demonstration of a single-step method for preparation of platelet concentrates was reported more than 25 years ago (deWit 1975). In this first attempt complete separation between the different cellular components could not be achieved, at least not in one step because of considerable overlap in the presence of platelets, leukocytes and erythrocytes in the fractions collected after different centrifugation times and speed. Many improved apheresis methods and devices have been developed and are described in cited patents.

In apheresis methods drawn blood is immediately mixed with an anticoagulant, centrifuged (Haemonetics, Baxter CS 3000 and Amicus, Cobe Spectra, Fresenius AS 104, AS 204), and separated into components according to density. The buffy coat is recognized by eye or by optical sensors and the platelet-rich layer is directed to a separate bag. Software of the various manufacturers has been adjusted to manufacture platelet concentrates without white cell contamination, some requiring additional filtration after the platelet harvest, others having special techniques or tools built into the apheresis systems.

Leukoreduction

The PC's resulting from both laboratory two spin processing and apheresis methods contain donor leukocytes. It was shown the white cells negatively affect platelet storage and may induce adverse effects after transfusion due to cytokine formation. Removal of leukocytes (leukoreduction) from PRP and PC is a major problem because non-self leukocytes (allogeneic leukocytes) and the cytokines they produce can cause a violent reaction by the recipient's leukocytes. In 1999 the FDA Blood Product Advisory Committee recommended routine leukoreduction of all non-leukocytes components in the US (Holme 2000). Therefore, much of the prior art focuses on leukoreduction of platelet concentrates because non-autologous leukocytes excite deleterious immune reactions. Since the process of this invention provides a convenient way to quickly harvest autologous platelets from the patient's blood, immune reactions are not a risk, and the presence of leukocytes is of little or no concern.

Autologous Platelets

Autologous platelets have been shown to have advantages in comparison with allogeneic platelets. Concerns about disease transmission and immunogenic reactions, which are associated with allogeneic or xenogeneic preparation, are minimized. The fact that an autologous preparation is prepared at the time of surgery reduces the risks associated with mislabeling a sample, which might occur through a laboratory system. The use of autologous platelets obviates the requirement for time-consuming screening tests. Platelet activation has less time to develop. Unlike stored platelets which become partially activated, the activation status of autologous platelets, when first produced, was found to be similar to that in the original whole blood (Crawther 2000).

Platelets may be used as an adjunct for wound healing. Knighton describes applying autologous platelet releasate to wounds to enhance healing (Knighton 1986). More recent studies use platelets themselves. Marx describes platelet preparations that dramatically accelerate bone healing following dental implant procedures (Marx 1998). Other researchers make similar claims for other medical procedures, for instance, treatment of macular holes (Gehring 1999), improved healing in cosmetic surgery (Man 2001), and use for hemostasis (Oz 1992).

In recent years devices originally invented to wash erythrocytes from shed blood (auto-transfusion devices) have been adapted to permit separation of autologous platelets, usually intraoperatively. This procedure has the important advantage that autologous leukocytes cause no reaction from patient leukocytes because they are self leukocytes, so removal of leukocytes from PC's is no longer important. For example, sequestration of PRP reduces allogeneic transfusion in cardiac surgery (Stover 2000). Auto-transfusion devices from a variety of manufacturers (e.g., ElectroMedics 500) can be used to make autologous platelet preparations with high platelet concentrations.

The auto-transfusion equipment used to make autologous platelet concentrates requires a skilled operator and considerable time and expense. Most devices require a large prime volume of blood. The ElectroMedics 500 withdraws 400 to 450 ml of autologous whole blood through a central venous catheter placed during surgery. As it withdraws the blood the separator adds citrate phosphate dextrose (CPD) to achieve anticoagulation. The blood is then centrifuged into its three basic components. The red blood cell layer forms at the lowest level, the platelet concentrate layer in a middle level, and the PPP layer at the top. The cell separator incrementally separates each layer, from the less dense to the more dense; therefore it separates PPP first (about 200 ml) and PC second (about 70 ml), leaving the residual red blood cells (about 180 ml). Once the PPP is removed, the centrifuge speed is lowered to 2400 RPM to allow for a precise separation of the PC from the red blood cells. In fact, the platelets most recently synthesized, and therefore of the greatest activity, are larger and mix with the upper 1 mm of red blood cells, so that this layer is included in the PRP product imparting a red tint.

Recently devices have been introduced which are specifically designed to make autologous platelet concentrates intraoperatively; for example the SmartPReP Autologous Platelet Concentrate System (Harvest Autologous Hemobiologics, Norwell, Mass.). It requires 90 to 180 cc of blood versus the 500 cc of blood used in most auto-transfusion machines. In addition two other products are near market introduction, The PlasmaSeal device (PlasmaSeal, San Francisco, Calif.) and The Platelet Concentrate Collection System (Implant Innovations, Inc., Palm Beach Gardens, Fla.). While these devices have somewhat reduced the cost and the time required, a skilled operator is required for the devices introduced to the market to date. Therefore, there remains a need for simple and fast automated methods and devices for making platelet concentrates.

SUMMARY

The present invention is directed to methods and apparatuses for simple and fast preparation of autologous platelet concentrates from whole anti-coagulated blood.

This discussion includes numerous descriptions of events within the spinning rotor. Within the frame of reference of the rotor, the effects of gravity are minimal compared with centrifugal force. Therefore within the rotor, "top" means the end of the tube closer to the axis and "bottom" means the end of the tube closer to the perimeter of the rotor.

Another aspect of the present invention is that platelets are not aggregated by pelleting against a surface.

A further aspect of the invention is the use of a float having a density less than the density of the erythrocytes and greater than that of whole blood which rises through the mixture as the erythrocyte sediment during centrifugation, gently disrupting the erythrocytes to free trapped platelets, thus greatly increasing the platelet yield.

Another aspect of the present invention is that the apparatuses may be completely automated and require no user intervention between, first, loading and actuating the device and, second, retrieving the platelet concentrate.

Another aspect of the present invention is that different quantities of blood may be processed by the same apparatus.

Another aspect of the present invention is that bloods of different hematocrits and different plasma densities may be processed by the same apparatus.

Another aspect of the present invention is that the concentration of platelets in the product may be varied by need.

Another aspect of the present invention is that the processing includes only a single centrifugation step.

Another aspect of the present invention is that the processing is rapid.

The float collector blood platelet separation device of this invention comprises a centrifugal spin-separator container having a separation chamber cavity with a longitudinal inner surface. A float is positioned within the cavity, the float having a base, a platelet collection surface above the base, and an outer surface. The distance between the outer surface of the float and the inner surface of the cavity can be 0.5 mm, preferably less than 0.2 mm and optimally less than 0.03 mm. The float has a density less than the density of erythrocytes and greater than the density of plasma. The platelet collection surface has a position on the float which places it immediately below the level of platelets when the float is suspended in fully separated blood. The cavity can have a cylindrical inner surface and the float has a complementary cylindrical outer surface.

In one embodiment, the device includes a flexible inner tube, and a float is positioned within the flexible inner tube. The float has an outer surface in sealing engagement with the inner surface of the flexible tube in a neutral pressure condition, the sealing engagement preventing movement of fluid between the outer surface of the float and the inner surface of the flexible tube in the neutral pressure condition. The outer surface of the float disengages from contact with the inner surface of the flexible tube in an elevated pressure condition, thus enabling movement of fluid between the outer surface of the float and the inner surface of the flexible tube in the elevated pressure condition as well as free movement of the float within the tube. The float has a platelet receptor cavity positioned to be at the position of platelets in separated blood after centrifugation. The float has a channel communicating with the platelet receptor cavity for removing separated platelets therefrom after centrifugation. In one configuration, the float comprises a proximal segment having a distal surface and a distal segment having a proximal surface opposed to the distal surface, the distal surface and the proximal surfaces defining the platelet receptor cavity. Preferably, the outer container includes a port for introducing blood into the inner tube at the beginning of a platelet separation process and for removing platelets from the platelet cavity within the inner tube at the end of the platelet separation process. Optionally, the port includes a syringe coupling Luer locking device. The outer container can have an inner surface for restraining expansion of the inner tube during centrifugation.

In a still further embodiment, the centrifugal spin-separator is a substantially rigid tube, and the float comprises a proximal segment having a distal surface, and a distal segment having a proximal surface opposed to the distal surface, the distal surface and the proximal surfaces defining the platelet receptor cavity. This cavity has a surface which is a platelet collection surface. The outer surface of the float is preferably in sliding engagement with the inner surface of the cavity.

The term "platelet collection surface", as used herein, is defined to mean a surface which provides support to the platelet or buffy coat layer. Preferably, the platelet layer is not in direct contact with the support layer to protect the platelets, and optimally, the platelets are sedimented on a thin buffer or cushion layer of erythrocytes resting on the platelet collection surface.

In another embodiment, a top surface of the float constitutes a platelet collection surface. In this form, the device may include a plunger positioned above the float and substantially axially concentric with the float and the cavity, the optional plunger having a cylindrical outer surface which is spaced from a complementary cylindrical inner surface of the tube. The space can be so small as to provide an effective liquid seal between the surfaces, or if the space is larger, at least one seal can be provided between the outer surface of the plunger and the inner surface of the cavity, the seal being positioned in sealing engagement with the outer and inner surfaces. Optionally, the bottom of the plunger has a plasma expressing surface opposed to the platelet collection surface; and a fluid removal passageway extends through the plunger and the plasma expressing surface into the platelet receptor cavity. Preferably, the top of the float includes a stop surface extending above the plasma collection surface.

The process of this invention for separating platelets from whole blood with the above devices comprises the steps of first introducing an amount of whole blood into the cavity, the amount of whole blood being sufficient, following centrifugation, to elevate the float above the floor of the separation chamber and position the platelet collection surface immediately below the level of platelets. The separation chamber is the cavity within which the blood is separated into erythrocyte, plasma and platelet (buffy coat) layers. The centrifugal spin-separator container is subjected to centrifugation forces in the axial direction toward the distal end, whereby erythrocytes are caused to concentrate at the distal end, plasma to collect toward the proximal end, and platelets to collect on the platelet collection surface. Platelets are then removed from the platelet collection surface.

When the device includes a plunger positioned above the float and substantially axially concentric with the float and the cavity, process of this invention comprises the steps of introducing an amount of whole blood into the cavity, the amount of whole blood being sufficient to position the level of platelets following centrifugation at the position of the platelet collection surface. The centrifugal spin-separator container is then subjected to centrifugation forces in the axial direction toward the distal end, whereby blood cells are caused to concentrate at the distal end, plasma to collect toward the proximal end, and platelets to collect closely adjacent the platelet collection surface. The plunger is then advanced in an axial direction against the top of the plasma until the plasma expressing surface is positioned closely adjacent the platelet collection surface and spaced apart therefrom. A platelet extraction tube is extended through the fluid removal passageway until the end thereof contacts the platelet layer, and a platelet concentrate is removed through the platelet extraction tube. Optionally, platelet poor plasma can be collected through the platelet extraction tube into a syringe or other receptacle while the plunger is being depressed. Platelets can then be extracted into a separate syringe or other receptacle.

Optionally, the device can lack a plunger arrangement. In this embodiment, platelets are removed from the platelet collection surface suspended in a small volume of plasma retained after first removing a volume of platelet poor plasma from above the sedimented platelet layer.

With embodiments of the device wherein the top of the float includes a stop surface positioned above the plasma collection surface, the plunger is advanced in an axial direction until the plasma expressing surface contacts the stop surface.

With devices having a float in a flexible tube, the process comprises the steps of introducing an amount of whole blood into the inner tube, the amount of whole blood being sufficient, following centrifugation, to elevate the float above the floor of the separation chamber and position the platelet collection surface immediately below the level of platelets. The tube is then subjected to centrifugation forces in the axial direction toward the distal end, whereby blood cells are caused to concentrate at the distal end, plasma to collect at the proximal end, and platelets to collect at a level closely adjacent the platelet collection surface. Platelets are then removed from the annular platelet receptor cavity.

When the top surface of the float constitutes the platelet collection surface, the device optionally includes a plunger positioned above the float and substantially axially concentric with the float and the cavity. The plunger has a cylindrical outer surface which is spaced from the inner surface of the cavity; the bottom of the plunger defining a plasma expressing surface opposed to a platelet collection surface. A fluid removal passageway extends through the plunger to the plasma expressing surface. With this embodiment, the process includes the additional step of moving the plunger toward the float until the plasma expressing surface is closely adjacent the platelet layer, and platelets are then removed through the fluid removal passageway. In this embodiment, plasma is expressed through the fluid removal passageway as the plunger is moved toward the float.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein:

FIG. 2 shows device of FIG. 1 wherein the plunger of the syringe is elevated, and the syringe barrel is filled with blood;

FIG. 3 shows device of FIG. 1 after the plunger is depressed to a position forcing the blood into the inner tube;

FIG. 4 shows device of FIG. 1 after a portion of the blood has passed between float and the inner tube, filling the bottom of the inner tube;

FIG. 5 shows device of FIG. 1 after the blood has separated into the erythrocyte fraction within which the float rests, the plasma fraction above the float, and the buffy coat or platelet layer in the receptor cavity;

FIG. 6 shows device of FIG. 1 after a fresh syringe has been connected to the Luer port;

FIG. 7 shows device of FIG. 1 with the syringe plunger elevated after drawing platelets from the receptor cavity into the barrel of the syringe;

FIG. 10 is a schematic cross-sectional view of the embodiment of FIG. 9 after introduction of anticoagulated blood into the separation chamber;

FIG. 11 is a schematic cross-sectional view of the embodiment of FIG. 9 after centrifugal separation of the blood into erythrocyte, plasma and platelet layers;

FIG. 12 is a schematic cross-sectional view of the embodiment of FIG. 9 after insertion of a syringe needle;

FIG. 13 is a schematic cross-sectional view of the embodiment of FIG. 9 after depression of the plunger to a level which abuts the float stop;

DETAILED DESCRIPTION

This invention is a blood platelet separation device with several embodiments. All of the embodiments comprise a centrifugal spin-separator container having a cavity with a longitudinal inner surface. A float is positioned within the cavity. The float has a base and a platelet collection surface above the base. The float has an outer surface. In general, the distance between the outer surface of the float and the inner surface of the cavity can be less than 0.5 mm, preferably less than 0.2 mm and optimally less than 0.03 mm. For embodiments with a flexible tube, the surfaces can be in contact. The platelet collection surface has a position on the float which places it immediately below the level of platelets when the float is suspended in fully separated blood.

Patient blood may be obtained by a phlebotomy needle or central vein cannula or other whole blood collection means. The blood is immediately mixed with anticoagulant, such as ACD-A or heparin.

Figure 1:
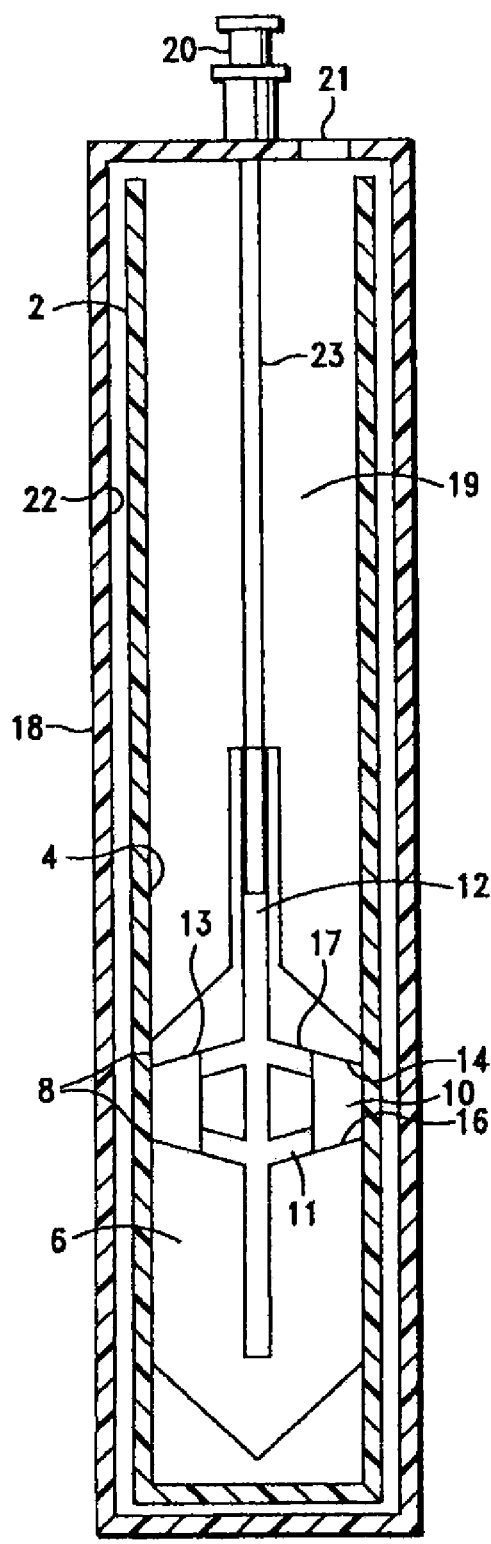
FIG. 1 is a schematic cross-sectional drawing of a separation device of this invention.

FIG. 1 is a schematic cross-sectional drawing of a separation device of this invention. The blood platelet collection device of this embodiment comprises a flexible inner tube 2 having an inner surface 4 and a float 6 positioned within the flexible inner tube. The float has an outer surface 8 in sealing engagement with the inner surface of the flexible tube when the tube is under neutral pressure. In this condition, the sealing engagement prevents movement of fluid between the outer surface of the float and the inner surface of the flexible tube.

The outer surface 8 of the float 6 disengages from contact with the inner surface 4 of the flexible tube 2 when the pressure in the flexible tube is elevated under centrifugation. This enables movement of fluid between the outer surface of the float and the inner surface of flexible tube as well as free movement of the float within the tube.

The float has a platelet receptor cavity 10 with a platelet collection surface 16 in a position to immediately below the level of platelets in separated blood following centrifugation. The float 6 has a platelet collection channel 11 and a platelet withdrawal channel 12 communicating with the platelet receptor cavity 10 for removing separated platelets after centrifugation.

The float 6 comprises a proximal segment 13 having a distal surface 14 and a distal segment 15 not having proximal surface 16 opposed to the distal surface 14. The distal surface 14 and proximal surface 16 define the platelet receptor cavity 10. The float 6 has a specific gravity that is less then the specific gravity of erythrocytes and greater than the specific gravity of plasma such that at equilibrium the buffy coat platelet layer is sequestered between the upper and lower members of the float. For optimum platelet recovery, it is critical that the float rise from the bottom of the tube as the erythrocytes sediment. This requires that the float have a density greater than whole blood.

The platelet collection device of this embodiment includes a substantially inflexible outer container 18 enclosing the inner tube 2. The inner surface 22 of the outer container 18 limits expansion of the inner tube as the pressure in the inner tube 2 increases during centrifugation.

The outer container includes a port 20 for introducing blood into the inner tube at the beginning of the platelet separation process and for removing platelets from the platelet receptor cavity 10 through channels 11 and 12 at the end of the platelet separation process. The port can be provided with a Luer lock device for coupling with a loading syringe and with a platelet removal syringe.

Vent channel 17 vents air upward through channel 12 as blood is introduced into the separation channel 19.

In this embodiment, the needle or small tube 23 is preferably fixed to the Luer lock device 20. The tube 23 has an outer diameter which is smaller than the inner diameter of the channel 12 to enable it to slide freely in the channel 12 as the float 6 rises during centrifugation.

The device of this invention can be used in a simple operation to produce platelets. It involves the collection of blood containing an anticoagulant such as heparin, citrate or EDTA in a syringe; filling the separation tubes with the anti-coagulated blood from the syringe; centrifugation to separate the blood into erythrocyte, plasma and platelet buffy coat fractions; and removal of the platelets buffy coat fraction with another syringe.

The float can be made of two cones, the bases thereof optionally concave. The separation chamber cavity preferably has a concave bottom which mirrors the shape of the lower cone so that when the buoy is in its initial state, resting at the bottom of the cavity, there is a small space between the bottom of the lower buoy and the bottom of the cavity. The flexible tube 2 is preferably an elastomer sleeve having an inner diameter which is smaller than the greatest outer diameter of the float so that it holds the float firmly in place. The outer diameter of the flexible tube 2 is smaller than the inner diameter of the rigid cylinder 18 so that a space exists between the inner tube and the rigid cylinder. Small particles such as smooth spheres, e.g., ball bearings, can be provided in the space between the two cones to disperse platelets in the platelet buffy coat layer. The channel 12 terminates slightly above the base of float 6. A sterile vent 21 allows air to pass in and out of the device.

FIGS. 2-7 are sequential schematic cross-sectional drawings of the device of this invention at the different phases of the separation process.

FIG. 2 shows the plunger 24 of the syringe 26 elevated, and the syringe barrel 28 is filled with blood 30.

FIG. 3 shows the plunger 24 depressed to a position forcing the blood 30 into the inner tube 2.

FIG. 4 shows the position after a portion of the blood 30 passes between float and the inner tube 2 during centrifugation, filling the bottom 32 of the inner tube.

FIG. 5 shows the blood components after centrifugation for a sufficient time to separate the blood components into the erythrocyte fraction 34 in which the float 6 floats, the plasma fraction 36 above the float 6, and the buffy coat or platelet layer 38 in the receptor cavity 10. Upon cessation of centrifugation, the blood remains fractionated into its three components, and the position of these components remains the same relative to the float. No longer under pressure produced by centrifugal force, the elastomer sleeve 2 has shrunk away from rigid cylinder 18 and locks the buoy in place.

Surprisingly, with the current invention, a much smaller fraction of platelets remain associated with the erythrocyte pack, making higher yields of sequestered platelets possible. The float rising from the bottom of the device as erythrocytes sediment fluidizes the erythrocyte pack to release the platelets so they more readily rise to combine with the buffy coat.

If re-suspension particles are present in the platelet receptor, the entire device can be shaken or rotated so that the particles tumble around within the space between the two cones, disrupting and mixing the buffy coat into a homogeneous suspension. Alternatively, the platelets can be re-suspended by jetting in and out of the platelet-containing compartment with the collection syringe. Alternatively, an air bubble can be trapped within or introduced into the platelet-containing compartment, and the platelets can be re-suspended by shaking, inverting or rolling the device. The suspended buffy coat is then withdrawn though the Lehr 20. The removed volume is displaced by air which enters the device through vent 21.

FIG. 6 shows the device with a fresh syringe 40 locked to the Luer port 20.

FIG. 7 shows the syringe plunger 42 elevated after drawing platelets 46 from above the platelet collection surface 16 in the receptor cavity 10 into the barrel 44 of the syringe. The suspended platelet layer has been withdrawn through the Luer 20. The removed volume is replaced by air which enters the device through a sterile vent 21 and further into the platelet receptor 10. The syringe 40 containing the platelets 46 is then removed for provision of the platelets to the physician treating a patient (not shown).

Figure 8:
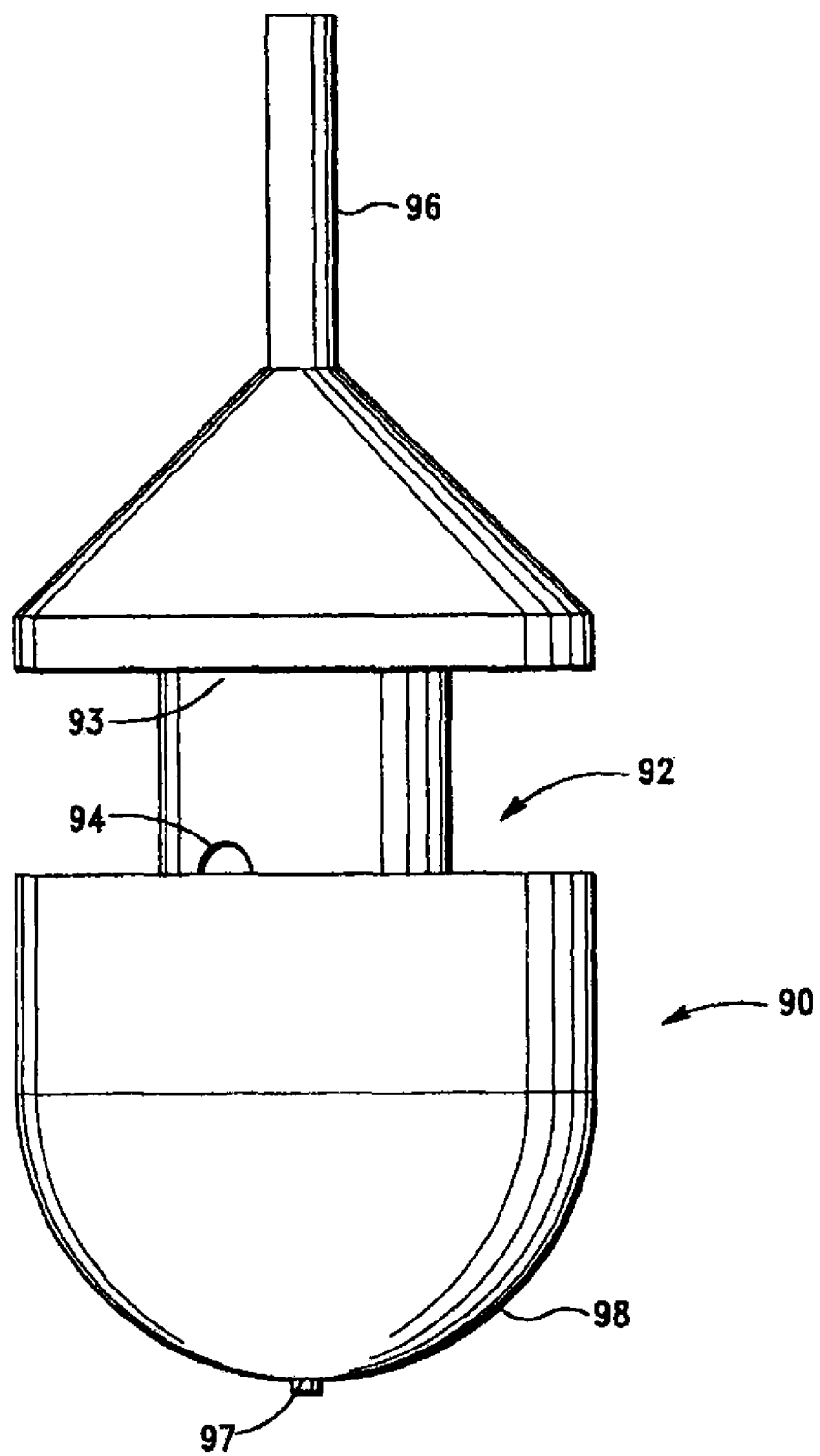
FIG. 8 is an isometric view of an alternative float design for the separation device of FIG. 1, the bottom of the float having a hemispherical shape.

FIG. 8 is an isometric view of the float component 90 with a platelet receptor 92, a vent channel 93 extending to the interior of the collection tube 96, and a platelet drainage channel 94 extending from the platelet receptor 92 to the interior of collection tube 96. This embodiment has a hemispherical bottom 98. The cylinder preferably has a concave bottom which mirrors the hemispherical bottom 98 so that when the buoy is in its initial state, resting near the bottom of the cylinder, space between the float and bottom are minimized. The projection 97 extending from the bottom of the hemispherical bottom 98 insures that a space is maintained between the bottom of the lower buoy and the bottom of the cylinder to prevent vacuum sticking of the float to the bottom of the tube.

Figure 9:
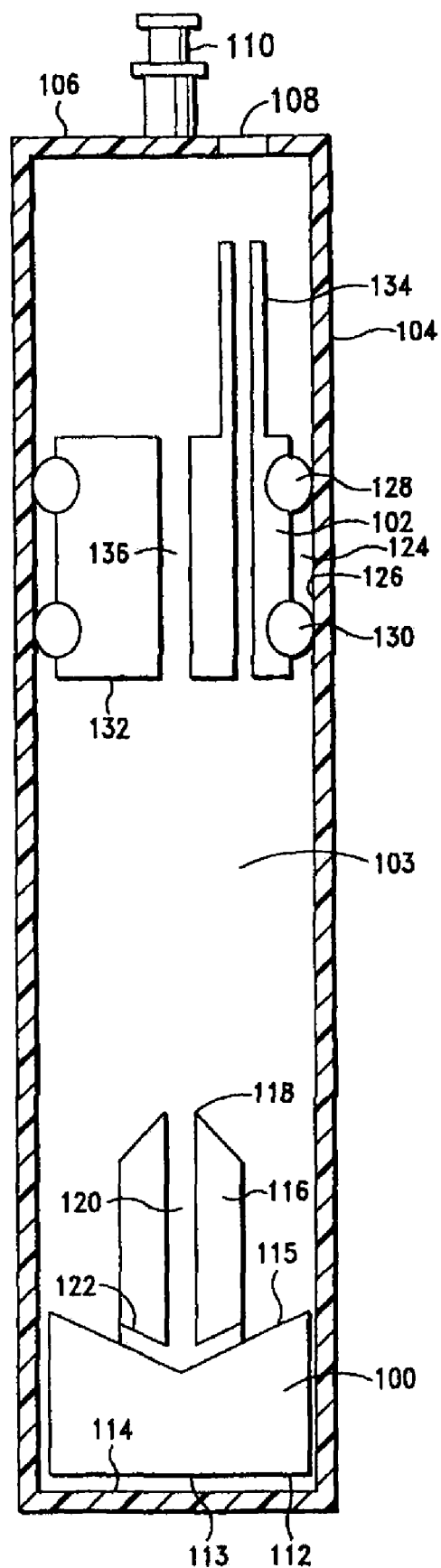
FIG. 9 is a schematic cross-sectional view of a plunger-float embodiment of the invention.

FIG. 9 is a schematic cross-sectional view of a plunger-float embodiment of the invention. In this embodiment, an axially concentric float 100 and plunger 102 are contained within the central cavity 103 of the rigid tube or cylinder 104 with a cap 106. The cap 106 has a vent hole 108 for permitting movement of air into and out of the tube when blood is added or platelets are removed. It includes a Luer port 110 for receiving a needle or tube used for introducing blood into the cylinder and for removing fluid from the cylinder.

The float 100 has a bottom surface 112 with a projecting spacer 113 which rests on the bottom 114 of the tube before anti-coagulated blood is introduced into the separator. The float has an upper surface 115 which is positioned to be immediately below the layer of platelets in separated blood. The upper structure of the float includes a projection 116, the top edge 118 of which acts as a stop to limit downward movement of the plunger 102 during the process. A platelet collection channel 120 is positioned in the center of the float. Platelet drainage channels 122 extend from the level of the surface 115 to the interior of the platelet collection channel 120.

The float 100 has a density less than separated erythrocytes and greater than plasma so that it will float on the erythrocyte layer at a level which places the platelet collection surface 115 immediately below the platelet layer when the blood is separated into its components. For optimum platelet recovery, it is critical that the float rise from the bottom of the tube as the erythrocytes sediment. This requires that the float have a density greater than whole blood.

The plunger 102 optionally can have an outer surface 124 which is spaced from the inner surface 126 of the tube 104 or in sliding engagement therewith. In the illustrated embodiment, seals 128 and 130 which can be O-rings are provided to prevent escape of liquid between the float and tube surfaces when the plunger 102 is moved toward the float 100. If the tolerances between the outer surface 124 and the tube surface 126 are sufficiently small, no seal is required to prevent escape of liquid between the plunger and the tube when the plunger is moved toward the float and when the product is withdrawn.

The plunger has a bottom surface 132 and a fluid escape or snorkel tube 134. When the plunger is moved downward toward the float, the pressure imparted by this bottom surface 132 expresses liquid below the plunger 102 upward through the snorkel tube 134 into the cavity above the plunger.

The plunger is provided with a central channel 136 through which a tube or needle is inserted to remove platelet-rich fluid from the space between the bottom of the plunger and the top of the float.

While this embodiment is illustrated with an outer tube and a float and plunger with matching outer cylindrical shapes, it will be readily apparent to a person skilled in the art that the outer container can have any internal shape which matches the dimensions of the float and plunger such as a cavity with a square or other polygonal shape combined with a float and plunger with the corresponding outer polygonal shape. The cylindrical configuration is advantageous.

FIG. 10 is a schematic cross-sectional view of the embodiment of FIG. 9 after introduction of anti-coagulated blood 138 into the separation chamber 103 through a tube 140 from a syringe 142.

FIG. 11 is a schematic cross-sectional view of the embodiment of FIG. 9 after centrifugal separation of the blood into erythrocyte 144, plasma 146 and platelet 148 layers. The float 100 has risen to place the platelet collection surface 115 immediately below the level of the platelets 148.

FIG. 12 is a schematic cross-sectional view of the embodiment of FIG. 9 after insertion of a syringe needle 150 of syringe 143 into the central channel 136 of plunger 102.

FIG. 13 is a schematic cross-sectional view of the embodiment of FIG. 9 after depression of the plunger 102 by pressing the syringe 143 downward, to a level which contacts its lower surface 132 with the stop tip 118 of the float 100. The plasma displaced by the plunger 102 has been expressed through the snorkel tube 134.

Withdrawal of the piston 150 of the syringe 143 draws a platelet-rich mixture from the platelet layer through the channels 122 and 120 (FIG. 9) and upward through tube 150 into the syringe tube 145. The position of the snorkel tube 134 above the liquid level provides for flow of air to fill the space created by removal of the platelet suspension.

Figure 14:
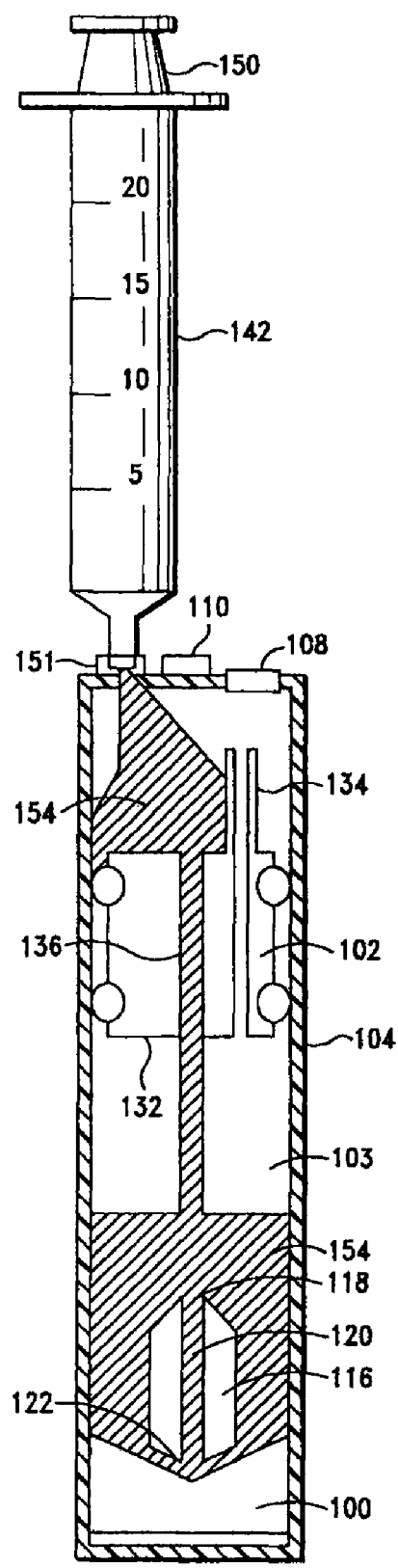
FIG. 14 is a schematic diagram view of an alternate embodiment related to the embodiment of FIG. 9 showing the introduction of blood through a separate fill port of the embodiment.

FIG. 14 is a variation of the embodiment shown in FIG. 9, with the addition of an optional port 151. This view shows blood 154 introduced through port 151 from syringe 142, flowing down channel 136 into the separation chamber 103.

Figure 15:
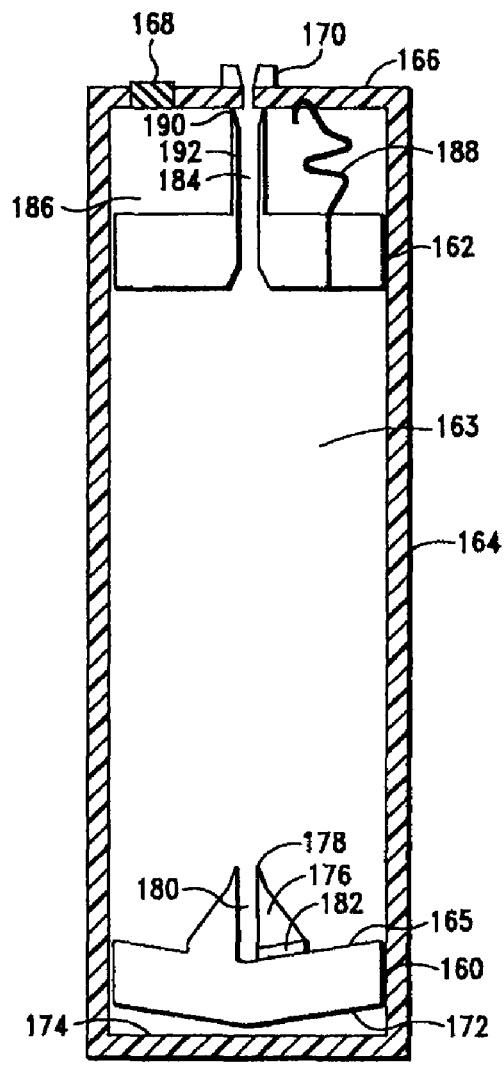
FIG. 15 is a schematic diagram of a still further alternate embodiment of a plunger-float device of this invention, including a flexible snorkel tube fixed to the cap.

FIG. 15 is a schematic cross-sectional view of a plunger-float embodiment of the invention. In this embodiment, an axially concentric float 160 and plunger 162 are contained within the separation chamber cavity 163 of rigid tube or cylinder 164 with a cap 166. The float has a platelet collection surface 165 which is positioned to be immediately below the layer of platelets in separated blood. The cap 166 has a vent hole 168 for permitting the escape of air from the tube when it blood is added to its interior. It also has a Luer 170 which receives a needle or tube for introducing blood into the separation chamber 163 and another needle or tube for removing fluid containing platelets from closely adjacent the platelet collection surface 165 following centrifugation.

The float 160 has a bottom surface 172 which rests on the bottom 174 of the tube before anti-coagulated blood is introduced into the separator. The upper structure of the float includes a projection 176, the top edge 178 of which acts as a stop to limit downward movement of the plunger 162 during the process. A platelet collection channel 180 in the center of the float communicates with platelet drainage channel 182 extending from the level of the surface 165.

The float 160 has a density less than separated erythrocytes and greater than plasma so that it will float in the erythrocyte layer at a level which places the platelet collection surface 165 immediately below the platelet layer when the blood is separated into its components. For optimum platelet recovery, it is critical that the float rise from the bottom of the tube as the erythrocytes sediment. This requires that the float have a density greater than whole blood.

As the plunger 162 is depressed toward the float 160 after centrifugation, plasma rises through the flexible snorkel tube 188 into the space 186 above the plunger 162. When platelets are removed by a tube extending through the central channel 184 (inserted as shown in FIG. 13), air flows through the tube 188 from its inlet at the top of the tube (above the liquid level) to replace the liquid being removed.

The plunger is shown at its highest level to permit introducing a maximum amount of blood into the separation chamber, the maximum height being limited by the top 190 of the tube 192 abutting the cap 166. This full extension is permitted by the flexibility of the snorkel tube 188.

Figure 16:
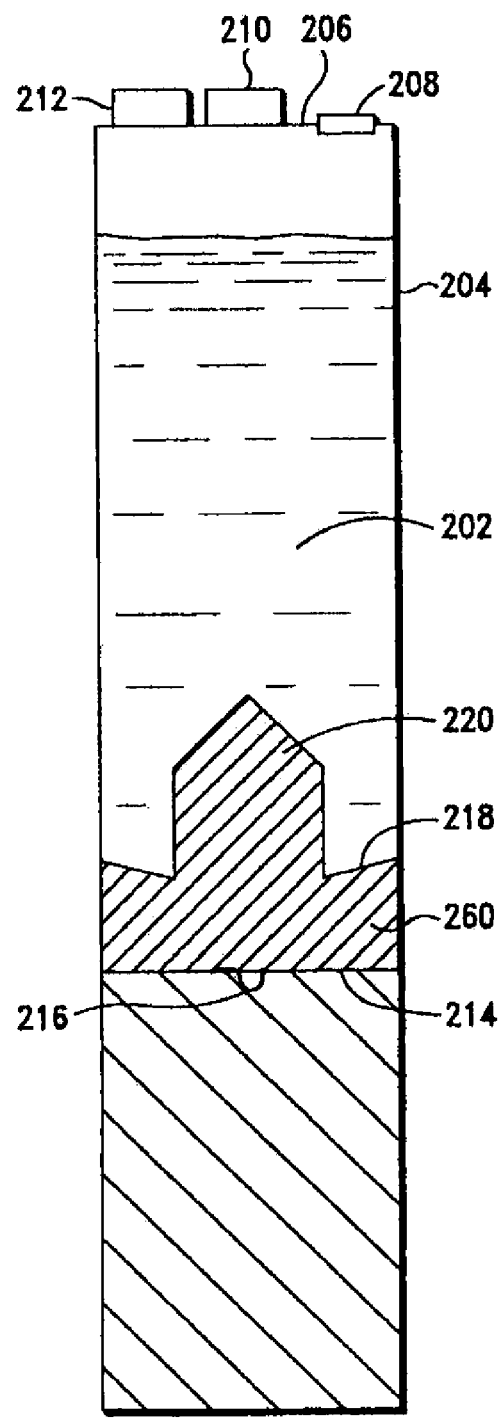
FIG. 16 is a schematic cross-sectional view of a plunger-float embodiment of the invention after centrifugation and before removal of the platelet layer.

FIG. 16 is a schematic cross-sectional view of a plunger-float embodiment of the invention after centrifugation and before removal of the platelet layer. In this embodiment, a float 200 is contained within the central cavity 202 of the rigid tube or cylinder 204 with a cap 206. The cap 206 has a vent hole 208 for permitting movement of air into and out of the tube when blood is added or platelets are removed. It includes a port 210 for receiving a needle or tube used for introducing blood into the cylinder and for removing fluid from the cylinder and a port 212 for receiving a syringe needle (not shown) for collecting platelets following centrifugation.

The float 200 has a bottom surface 214 with a projecting spacer 216 which rests on the bottom of the tube before anti-coagulated blood is introduced into the separator. The float rises in the erythrocyte layer during centrifugation. The float 200 has an upper surface 218 which is positioned to be immediately below the layer of platelets in separated blood. The upper structure of the float includes a projection 220 which extends above the platelet or buffy coat layer.

The float 200 has a density less than separated erythrocytes and greater than plasma so that it will float in the erythrocyte layer at a level which places the platelet collection surface 218 immediately below the platelet layer when the blood is separated into its components. For optimum platelet recovery, it is critical that the float rise from the bottom of the tube as the erythrocytes sediment. This requires that the float have a density greater than whole blood.

The "Plungerless plunger" device of FIG. 16 is the simplest and cheapest to manufacture. The user can vary the platelet concentration factor simply by removing more or less platelet poor plasma before re-suspending the platelets. It requires more user attention and care to accurately remove the desired amount of platelet poor plasma. The parasol float system of FIG. 1 and the plunger-float system of FIG. 9 provide better reproducibility than the simple float embodiment of FIG. 16.

This invention is further illustrated by the following specific, but non-limiting examples.

Example 1

Parasol Float Device

A parasol design platelet concentrator device of the type depicted in FIG. 1 was constructed. The float was comprised of polyethylene and polycarbonate in such proportion as to have an overall density of 1.06 g/ml. The outer diameter of the float was 2.62 cm and its overall length was 4.57 cm. The float together with two stainless steel balls 0.32 cm in diameter in the platelet receptor cavity was inserted into the sealed end of a flexible silicone rubber tube. The flexible tube had an inner diameter of 2.54 cm, a wall thickness of 0.08 cm, and a sealed distal end. The flexible tube containing the float was housed within a rigid polycarbonate tube with inner diameter of 2.86 cm and length 11.43 cm. The top of the flexible tube was folded over the top of the rigid tube and a cap with a 7.62 cm tube 23 (see FIG. 1) was fitted over the folded top of the flexible tube with tube 23 engaging channel 12.

The device was filled with 30 ml of freshly drawn whole blood anti-coagulated with CPDA-1. The device was centrifuged in an IEC Centra CL2 centrifuge for 30 minutes at 3000 rpm. Following centrifugation the tube was swirled vigorously to re-suspend the platelets within the platelet receptor cavity by the agitation induced by the stainless steel balls. Five cc concentrated platelets was removed from the platelet receptor cavity through the platelet extraction tube (23).

Platelet counts were determined as follows: One half cc of this sample was diluted with 10 cc of Isoton II isotonic diluent and centrifuged at 500 g for 1.5 minutes. One half cc of this diluted sample was diluted in yet another 10 cc of Isoton II and particles larger than 3 fl counted on a Coulter Z-1 particle analyzer. This result was compared to the number of particles in a similarly treated sample of whole blood. These small particles from treated samples represent the platelets. The sample of concentrated platelets contained 66% of the platelets present in the introduced whole blood at a concentration 2.86 times that found in the whole blood.

The "Parasol" device shown in FIG. 1 is most difficult and expensive to manufacture, but is easiest to use. The erythrocyte concentration is more variable with this product. This results from different plasma densities, and hematocrit-dependant variability is present in the amount of displacement of fluid by contraction of the elastomeric sleeve during deceleration.

Example 2

Plunger-Float Device with Snorkel

A platelet concentrator device of the type depicted FIG. 9 was constructed. The float was comprised of polyethylene and polycarbonate in such proportion as to have an overall density of 1.08 g/ml. The outer diameter of the float was 2.535 cm and its overall length was 1.2 cm. The float was inserted into a rigid polycarbonate tube with an inner diameter of 2.540 cm and length 11.43 cm. The bottom of the rigid tube was sealed.

The device was filled with 25 cc of freshly drawn whole blood anti-coagulated with CPDA-1. The device was centrifuged in an IEC CRU 5000 centrifuge for 15 minutes at 1800 rpm. Following centrifugation the plunger was depressed by inserting a blunt hypodermic needle connected to a 10 cc syringe through the central access port until it collided with the stop on the top of the float. The device was swirled vigorously to re-suspend the platelets within the platelet receptor cavity after withdrawing 0.5 cc through the hypodermic needle (platelet extraction tube). An additional 3.5 cc concentrated platelets was removed from the platelet receptor cavity through the hypodermic needle (platelet extraction tube).

One half cc of this sample was diluted with 10 cc of Isoton II isotonic diluent and centrifuged at 500 g for 1.5 minutes. One half cc of this diluted sample was diluted in yet another 10 cc of Isoton II and particles larger than 3 fl counted on a Coulter Z-1 particle analyzer. This result was compared to the number of particles in a similarly treated sample of whole blood. These small particles from treated samples represent the platelets. The sample of concentrated platelets contained 69% of the platelets present in the introduced whole blood at a concentration 4.30 times that found in the whole blood.

The "Plunger" device shown in FIG. 9 has advantage of being cheap to manufacture and having less variability in percent erythrocytes in the product. The plunger-float combination provides a greater concentration factor because the volume between plunger and float can be smaller and still accommodate the entire range of plasma densities while keeping the level of the buffy coat within the gap. Erythrocyte contamination is independent of hematocrit.

Example 3

Plunger-Float Device without Snorkel

A platelet concentrator device of the type depicted in FIG. 9 was constructed, except without the snorkel tube so that the only fluid communication between the space below the plunger and the space above the plunger was through a platelet receptor cavity. The float was comprised of polyethylene and polycarbonate in such proportion as to have an overall density of 1.08 g/ml. The outer diameter of the float was 2.535 cm and its overall length was 1.2 cm. The float was inserted into a rigid polycarbonate tube with an inner diameter of 2.540 cm and length 11.43 cm. The bottom of the rigid tube was sealed.

The device was filled with 25 cc of freshly drawn whole blood anti-coagulated with CPDA-1. The device was centrifuged in an IEC CRU 5000 centrifuge for 15 minutes at 1800 rpm. Following centrifugation, the plunger was depressed by inserting a blunt hypodermic needle connected to a 10 cc syringe through the central access port and pressing down on the body of the syringe until it collided with the stop on the top of the float. As the syringe body was depressed, platelet poor plasma collected in it. The syringe containing platelet poor plasma was removed and a second syringe was attached to the needle. The device was swirled vigorously to re-suspend the platelets within the platelet receptor cavity after withdrawing 0.5 cc through the hypodermic needle (platelet extraction tube). An additional 3.5 cc concentrated platelets was removed from the platelet receptor cavity through the hypodermic needle (platelet extraction tube).

One half cc of this sample was diluted with 10 cc of Isoton II isotonic diluent and centrifuged at 500 g for 1.5 minutes. One half cc of this diluted sample was diluted in yet another 10 cc of Isoton II and particles larger than 3 fl counted on a Coulter Z-1 particle analyzer. This result was compared to the number of particles in a similarly treated sample of whole blood. These small particles from treated samples represent the platelets. The sample of concentrated platelets contained 74% of the platelets present in the introduced whole blood at a concentration 4.61 times that found in the whole blood. Since this concentration is much larger and the concentration of platements in the erythrocyte layer is much lower than obtained with simple centrifugation under comparable conditions without the float, it is clear that the flow of erythrocyte suspension between the walls of the float and the tube during centrifugation gently disrupts the erythrocytes and releases entrapped platelets, allowing them to collect in the platelet or buffy-coat layer.

With the "Plunger" device without snorkel used in this example, the platelet poor plasma is collected in a syringe during depression of the plunger. This provides all the advantages of "standard" plunger device plus providing platelet poor plasma in syringe for anyone who might want to use it, for example, as a hemostat.

Various alternative configurations of the device are possible within the context of the present invention. For example, the two cones which comprise the buoy can be replaced by funnels or by cones possessing concavities that communicate between the various compartments and conduct sedimenting cells between compartments during sedimentation. Complete fluid isolation of the various compartments is not essential, provided any openings between compartments are sufficiently small as to prevent substantial mixing of the fractions during handling and re-suspension and withdrawal of the buffy coat. Means can be provided for recovery of platelet depleted plasma and erythrocytes if desired. The tube and the channel through which blood is introduced and the buffy coat is withdrawn need not be concentric or rigid. The elastomeric sleeve can be replaced by a compressible material, e.g., foam, provided the inner surface which contacts blood is smooth and does not trap or activate platelets.

What is claimed is:

1. A method for separating platelets from blood for application to a patient in a medical treatment, comprising:
    placing the blood in a container having a sidewall and a bottom at least partially defining a volume;
    positioning a float that has a surface that defines a collection area within the volume of the container;
    providing a force on the float and the blood;
    causing the float to move from near the bottom of the container within the volume due at least in part to the force provided on the float;
    sedimenting platelets from the blood placed in the container on a thin layer of erythrocytes resting on the surface of the float in the container within the volume; and
    accessing the volume through at least one of two access ports passing through a top wall at a top end of the container.

2. The method of claim 1, further comprising:
    subjecting the container having the blood placed therein to a centrifugal force;
    wherein platelets suspended in plasma of the blood are sedimented on the thin layer of erythrocytes by centrifugal force.

3. The method of claim 1, wherein the surface is an upper surface of a platelet collection surface.

4. The method of claim 1, further comprising:
    centrifuging plasma containing erythrocytes and platelets to sediment platelets on at least a portion of the erythrocytes.

5. A method for separating platelets from blood for application to a patient in a medical treatment, comprising:
    placing the blood in a container having a sidewall and a bottom at least partially defining a volume;
    sedimenting platelets from the blood placed in the container on a thin layer of erythrocytes resting on a surface in the container within the volume;
    accessing the volume through at least one of two access ports passing through a top wall at a top of the container;
    positioning a float within the volume of the container;
    providing a force on the float and the blood;
    causing the float to move within the volume due at least in part to the force provided on the float; and
    defining a collection area with the float, wherein defining a collection area includes: providing an outer rim of the float having a first height and providing a top wall of the float defining a depressed center having a point below the first height of the outer rim;
    wherein sedimenting the platelets includes sedimenting the erythrocytes near the surface of the float near the collection area on the thin layer of erythrocytes.

6. The method of claim 1, further comprising:
    providing the float of only polyethylene and polycarbonate.

7. The method of claim 1, further comprising:
    providing the float of only a substantially rigid material; and
    fixing the float at a selected position within the provided container in the absence of the force.

8. A method for separating platelets from a blood volume for application to a patient in a medical treatment, comprising:
    providing a container having a sidewall and a bottom at least partially defining a container volume;
    positioning a first member within the container volume;
    providing a cap with at least two access ports in the cap on the container;
    placing the blood volume in the container volume;
    providing a force on the blood volume to move the first member;
    allowing a portion of the blood volume to pass through an opening in the first member;
    separating erythrocytes from the blood volume;
    forming the first member to have a density to allow the first member to move from near the bottom of the container to a position near the erythrocytes separated from the blood volume to allow formation of a thin layer of erythrocytes on a surface of the first member; and
    sedimenting platelets on the thin layer of erythrocytes resting on the surface; and
    accessing the sedimented platelets through at least one of the two access ports in the cap.

9. The method of claim 8, further comprising:
    centrifuging the container, the first member, and the blood volume;
    wherein platelets suspended in plasma are sedimented on the thin layer of erythrocytes by centrifugal force.

10. A method for separating platelets from a blood volume for application to a patient in a medical treatment, comprising:
    providing a container having a sidewall and a bottom at least partially defining a container volume;
    positioning a first member within the container volume;
    positioning a second member in the container;
    placing the blood volume in the container volume;
    providing a force on the blood volume to move the first member;
    allowing a portion of the blood volume to pass through an opening in the first member;
    moving the second member through the portion of the blood;
    separating erythrocytes from the blood volume;
    forming the first member to have a density to allow the first member to move from near the bottom of the container to a position near the erythrocytes separated from the blood volume to allow formation of a thin layer of erythrocytes on a surface of the first member;
    sedimenting platelets on the thin layer of erythrocytes resting on the surface;
    orienting the container in a selected manner; and
    moving a limited portion of the blood volume to a first section of the container volume separated from a second section of the container volume.

11. The method of claim 10, wherein orienting the container in a selected manner includes moving the second member from a first position to a second position.

12. The method of claim 10, further comprising: allowing the limited portion of the blood volume to pass through an opening in the second member at least by pushing the second member through the container with an exterior force, including allowing at least a plasma portion of the blood volume that has separated in the container to move to the first section.

13. The method of claim 12, further comprising:
    fixing the second member within the container at a selected location when the force is not provided.

14. The method of claim 8, further comprising:
withdrawing the blood volume from a patient prior to placing the blood volume in the container volume;
moving a first side of the first member past at least a portion of the erythrocytes from the blood volume; and
maintaining a selected portion of the erythrocytes on the first side of the first member;
wherein sedimenting the platelets includes sedimenting the platelets on the maintained selected portion of the erythrocytes.

15. A method for separating platelets from blood for application to a patient in a medical treatment, comprising:
providing a container;
positioning the blood in the container by delivering the blood into the container through a first port in a first end wall of the provided container;
providing a force to separate the blood;
moving a float from a first position to a second position to assist in separating the blood;
after moving the float to the second position, moving at least a portion of the separated blood to a selected section of the container away from the float in the second position;
moving a member in the provided container through at least a portion of the blood relative to the float; and
withdrawing a portion of the separated blood from the container through a second port in the first end wall of the provided container;
wherein withdrawing a portion of the separated blood from the container through the second port includes withdrawing the portion from a layer from between the float and the member.

16. The method of claim 15, wherein the second port is positioned to allow access to the selected section of the container.

17. A method for separating platelets from blood for application to a patient in a medical treatment, comprising:
providing a container;
positioning the blood in the container;
providing a force to separate the blood;
moving a float from a first position to a second position to assist in separating the blood; and
after moving the float to the second position, moving at least a portion of the separated blood to a selected section of the container away from the float in the second position;
wherein moving at least a portion of the separated blood includes moving a member in the provided container and through at least a portion of the blood after separating the blood.

* * * * *

UNITED STATES PATENT AND TRADEMARK OFFICE
CERTIFICATE OF CORRECTION

| | | |
|---|---|---|
| PATENT NO. | : 7,837,884 B2 | |
| APPLICATION NO. | : 12/344895 | |
| DATED | : November 23, 2010 | |
| INVENTOR(S) | : Dorian et al. | |

It is certified that error appears in the above-identified patent and that said Letters Patent is hereby corrected as shown below:

Title Page, References Cited, Other Publication, pg. 5, col. 2, reference 4, After "Natural", delete "i".

Title Page, References Cited, Other Publication, pg. 6, col. 1, reference 9, "123:97-106" should be --23:97-106--.

Column 1, line 45, "a nuclear" should be --anuclear--.

Column 3, line 19, after "can", insert --be--.

Column 4, line 58, "PC's" should be --PCs--.

Column 5, line 39, "PC's" should be --PCs--.

Column 10, line 18, after "position", delete "to".

Column 10, line 28, "then" should be --than--.

Column 11, line 49, "though the Lehr 20" should be --through the Luer 20--.

Column 13, line 37, delete "it" before "blood".

Column 16, line 45, "platements" should be --platelets--.

Signed and Sealed this
Twenty-third Day of August, 2011

David J. Kappos
*Director of the United States Patent and Trademark Office*